US005716603A

United States Patent [19]
Chen et al.

[11] Patent Number: 5,716,603
[45] Date of Patent: Feb. 10, 1998

[54] AQUEOUS NAIL POLISH COMPOSITIONS CONTAINING ACRYLIC RESINS CROSSLINKED WITH ACRYLATED URETHANE OLIGOMERS

[75] Inventors: Robert Gowsheng Chen; David Lee Hutchins, both of Kingsport, Tenn.

[73] Assignee: Eastman Chemical Company, Kingsport, Tenn.

[21] Appl. No.: 550,266

[22] Filed: Oct. 30, 1995

Related U.S. Application Data

[60] Provisional application No. 60/000,349 Jun. 20, 1995.
[51] Int. Cl.⁶ .............................. A61K 7/04; A61K 7/043
[52] U.S. Cl. ................................ 424/61; 424/78.03
[58] Field of Search ........................ 424/61, 401, 78.03

[56] References Cited

U.S. PATENT DOCUMENTS

| | | | |
|---|---|---|---|
| 3,483,289 | 12/1969 | Michaelson | 424/61 |
| 3,927,203 | 12/1975 | Seymour et al. | 424/61 |
| 4,097,589 | 6/1978 | Shansky | 424/61 |
| 4,126,675 | 11/1978 | Boulogne et al. | 424/61 |
| 4,158,053 | 6/1979 | Greene et al. | 424/61 |
| 4,384,058 | 5/1983 | Galante | 524/32 |
| 4,409,203 | 10/1983 | Gordon et al. | 424/61 |
| 4,596,260 | 6/1986 | Giuliano | 132/73 |
| 4,682,612 | 7/1987 | Giuliano | 132/73 |
| 4,704,303 | 11/1987 | Cornell | 424/61 |
| 5,057,312 | 10/1991 | Langla et al. | 424/81 |
| 5,118,495 | 6/1992 | Natziger | 424/61 |
| 5,120,529 | 6/1992 | Koch et al. | 424/61 |
| 5,266,322 | 11/1993 | Myers et al. | 424/401 |
| 5,380,520 | 1/1995 | Dobbs | 424/61 |
| 5,407,666 | 4/1995 | Patel | 424/61 |
| 5,456,905 | 10/1995 | Valenty | 424/61 |
| 5,508,027 | 4/1996 | Witbeck | 424/61 |
| 5,601,808 | 2/1997 | Mellul | 424/61 |

FOREIGN PATENT DOCUMENTS

| | | | |
|---|---|---|---|
| 0 424 112 | 4/1991 | European Pat. Off. | A61K 7/043 |
| 2-221214 | 9/1990 | Japan | A61K 7/043 |
| 5-163118 | 6/1992 | Japan | A61K 7/043 |
| 4-297409 | 10/1992 | Japan | A61K 7/043 |
| 6-298624 | 10/1994 | Japan | A61K 7/043 |

OTHER PUBLICATIONS

Derwent Abstract, Japanese 3–133916, Jun. 1991.
Derwent Abstract, German 3937231, May 1991.
EP,A,0 453 628 (Heraeus Kulzer GmbH) 30 Oct. 1991.
EP,A,0 593 959 (Hüttenes–Albertus Chemische–Werke) 27 Apr. 1994.
STN, File Supplier, Karlsruhe, DE, File XP002015007; Chemical Abstracts, vol. 113, n 178027 & JP,A,02 019 313 (International Beauty Distributors) 23 Jan. 1990.

*Primary Examiner*—Sally Gardner-Lane
*Attorney, Agent, or Firm*—Andrew B. Griffis; Harry J. Gwinnell

[57] ABSTRACT

This invention relates to an aqueous acrylic resin crosslinked with difunctional acrylated urethane oligomers which are used in nail polish compositions. The nail polish compositions exhibit quick dry time, excellent leveling, good water/detergent resistance, abrasion resistance and durability with good adhesion to nails for long-wear nail polish applications and yet are easily removed from the nail.

17 Claims, No Drawings

AQUEOUS NAIL POLISH COMPOSITIONS CONTAINING ACRYLIC RESINS CROSSLINKED WITH ACRYLATED URETHANE OLIGOMERS

CROSS REFERENCE TO RELATED APPLICATIONS

This application claims the benefit of provisional application Ser. No. 60/000,349, filed on June 20, 1995.

1. Field of the Invention

This invention relates to aqueous nail polish compositions containing highly branched, partially crosslinked aqueous acrylic resins with difunctional acrylated urethane oligomers.

2. Background of the Invention

The conventional film forming agents used in nail polishes are solvent-based lacquers prepared from nitrocellulose which form high gloss films on nails. Unmodified nitrocellulose nail polishes, however, tend to lift off the nail and are subject to yellowing with age during storage due to their chemical instability. Moreover, unmodified nitrocellulose nail polishes create allergenic problems for some users.

To overcome the problems associated with unmodified nitrocellulose nail polishes, nitrocellulose nail polishes have been modified by incorporation of a formaldehyde resin such as an aryl sulfonamide formaldehyde resin. However, formaldehyde resins tend to dry the nail and make it brittle. Moreover, formaldehyde resins create allergenic problems for some users due to the liberation of formaldehyde.

Examples of various film formers which have been used in solvent-based nail polish formulations are disclosed in U.S. Pat. Nos. 5,057,312, 4,384,058, 4,409,203, 4,126,675, and 3,927,203. U.S. Pat. No. 5,057,312, discloses a copolymer containing units resulting from the copolymerization of at least one alkyl acrylate or methacrylate, and at least one hydroxyalkyl acrylate or hydroxyalkyl methacrylate. U.S. Pat. No. 4,384,058 discloses a film forming agent, a compatible solvent, and an auxiliary resin selected from alkyl cyanoacrylate and styrene-acrylonitrile-acrylic terpolymer. U.S. Pat. No. 4,409,203 discloses the use of ethyl methacrylate and cellulose acetate propionate. U.S. Pat. No. 4,126,675 discloses the use of a copolymer of methyl. methacrylate and hexyl methacrylate. U.S. Pat. No. 3,927,203 discloses the use of a copolymer of at least one alkoxy alkyl acrylate or methacrylate with at least one different alkoxy alkyl acrylate or methacrylate or at least one hydroxy alkyl acrylate or methacrylate.

The solvent-based nail polishes cause yellowing of the nail, contain a significant amount of volatile organic compounds which cause health and environmental concerns, and require long drying times due to the plasticizer or slow evaporating solvents used in the formulations.

In order to overcome the disadvantages of solvent-based nail polish formulations, attempts have been made to develop film forming resin systems by emulsion polymerization which can be used in water-based nail polishes. U.S. Pat. No. 4,158,053 discloses polymers prepared by emulsion polymerization of an alkyl acrylate, alkyl methacrylate, and/or styrene. U.S. Pat. No. 5,266,322 discloses film forming compositions prepared from an aqueous emulsion containing a sulfopolyester and a copolymer of vinyl acetate and dialkyl maleate, and an aqueous emulsion containing acetoacetoxyethyl methacrylate and a vinyl monomer.

Japan Patent No. 5,163,118 discloses a resin which is obtained by emulsion polymerization of a reactive surfactant and one or more monomers selected from ethylenically unsaturated carboxylic acid, methacrylic ester, acrylic ester, and styrene.

German patent No. 3937231 A1 discloses the use of a mixture from polyurethane emulsions and acrylic emulsion polymers. U.S. Pat. No. 5,120,529 discloses a water-based nail polish which contains 12–50% by weight of polyurethane and/or a polyurethane/acrylate copolymer in dispersed form, 0.1 to 1% of a thickener, and water. The polyurethane/acrylate copolymers in dispersed form are prepared by emulsion polymerization of water dispersible polyurethane with acrylic co-monomers.

Disadvantages associated with the use of emulsion polymers in nail polish formulations include poor freeze-thaw stability and the necessity of adding a water soluble thickener. The incorporation of pigments in such nail polish formulations is also very difficult and requires the use of additional surfactant and/or water soluble dispersant which further impairs the nail polish's water/detergent resistance. In addition, evaporation of water causes the emulsion particles to fuse together and deposit in the neck of the nail polish bottle.

Nail polishes containing water reducible or water dispersible acrylic resins are disclosed in Japan Patent No. 2,221, 214. The nail polishes are prepared by solution polymerization of 0.5–15 wt % of salt-forming group-containing monomers and 85–99.5 wt % of copolymerizing monomers in organic solvent, neutralizing the salt-forming groups with triethyl amine, and mixing with water. These polymers are sensitive to water and detergent because of their hydrophilic salt-forming groups. In addition, due to the lower molecular weight, <200,000, of these polymers, their abrasion resistance and durability characteristics are usually poor in comparison with other high molecular weight polymers. Furthermore, nail polishes prepared from these polymers tend to lose gloss with time.

SUMMARY OF THE INVENTION

The aqueous nail polish of the present invention overcomes the disadvantages of previous nail polish compositions by crosslinking an acrylic resin with difunctional acrylated urethane oligomer, said aqueous nail polish composition having a solid level of 15 to 35 percent, a Tg of $-10°$ C. to $70°$ C., and a weight average molecular weight of 5,000 to 180,000, said aqueous nail polish composition comprising:

(1) 0.1 to 15 weight percent of a difunctional acrylated urethane oligomer;

(2) 2 to 20 weight percent of an $\alpha,\beta$-ethylenically unsaturated carboxylic acid monomer containing 3 to 10 carbon atoms;

(3) 8 to 75 weight percent of an acrylate ester having the formula $CH_2=CH-COOR_1$, wherein $R_1$ is selected from the group consisting of $C_1-C_{20}$ alkyl, phenyl, benzyl, hydroxy-$(C_1-C_4)$-alkyl, $C_1-C_4$ alkoxy-$(C_1-C_4)$ alkyl, cyclopentyl, cyclohexyl, furyl, $C_1-C_4$ alkylfuryl, tetrahydrofuryl, and $C_1-C_4$ alkyltetrahydrofuryl; and (4) 8 to 75 weight percent of a methacrylate ester having the formula $CH_2=C(CH_3)-COOR_2$, wherein $R_2$ is selected from the group consisting of $C_1-C_{20}$ alkyl, phenyl, benzyl, hydroxy-$(C_1-C_4)$-alkyl, $C_1-C_4$ alkoxy-$(C_1-C_4)$ alkyl, cyclopenyl, cyclohexyl, furyl, $C_1-C_4$ alkylfuryl, tetrahydrofuryl, and $C_1-C_4$ alkyltetrahydrofuryl;

wherein the aqueous nail polish composition is prepared by solution polymerization at a temperature of $50°$ C. to $130°$ C. in the presence of at least one water miscible solvent and an initiator, and the weight percents are based on the total weight of the nail polish.

DETAILED DESCRIPTION OF THE INVENTION

The aqueous nail polish compositions of this invention are partially crosslinked acrylic resins with difunctional acrylated polyurethane oligomers prepared by solution polymerization of a difunctional acrylated urethane oligomer, an α,β-ethylenically unsaturated carboxylic acid monomer containing 3 to 10 carbon atoms, an acrylate ester, and a methacrylate ester. The solution polymerization is conducted in the presence of at least one water miscible solvent and an initiator.

Component (1) of the nail polish composition is a difunctional acrylated urethane oligomer which is present in an amount of 0.1 to 15 weight percent, preferably 2 to 10 weight percent based on the weight of the nail polish composition. The difunctional acrylated urethane oligomer is prepared by reacting an hydroxy acrylate or hydroxy methacrylate; a hydroxyl-terminated diol, polyester, or diamine; and a diisocyanate.

Preferred hydroxy acrylates and hydroxy methacrylates are selected from: 2-hydroxyethyl acrylate, 2-hydroxyethyl methacrylate, hydroxypropyl acrylate, and hydroxypropyl methacrylate. Preferred diisocyanates are selected from: dicyclohexylmethane 4,4'-diisocyanate, isophorone diisocyanate, and toluene diisocyanate. Preferred hydroxyl-terminated diols are selected from: ethylene glycol, propane diol, neopentyl glycol, butane diol, hexane diol, 1,4-cyclohexanediol, and 4,4'-dihydroxy cyclohexyl 2,2-propane. Preferred polyesters are selected from bis (ethoxylated) Bisphenol A, bis(propoxylated) Bisphenol A, polyethylene oxide diol, polypropylene oxide diol, and polyester diol. Preferred diamines are selected from ethylene diamine, 1,2-propylene diamine, 1,8-methane diamine, and isophorone diamine. Suitable difunctional acrylated urethane oligomers are commercially available from Sartomer, Inc., under the trade names SARTOMER CN-953®, CN-964®, CN-965®, CN-980®, CN-972® and CN-981®.

Component (2) of the nail polish composition is an α,β-ethylenically unsaturated carboxylic acid monomer containing 3 to 10 carbon atoms. The α,β-ethylenically unsaturated carboxylic acid monomer is present in an amount of 2 to 20 weight percent, preferably 4 to 15 weight percent based on the total weight of the nail polish composition. Examples of α,β-ethylenically unsaturated carboxylic acid monomers include acrylic acid, methacrylic acid, crotonic acid, fumaric acid, itaconic acid, and maleic anhydride. Preferably the α,β-ethylenically unsaturated carboxylic acid monomer is selected from acrylic acid, methacrylic acid, and maleic anhydride. Combinations of α,β-ethylenically unsaturated carboxylic acid monomers may also be used.

The presence of the α,β-ethyleniclly unsaturated carboxylic acid in the nail polish composition allows for the use of pigments without requiring auxiliary dispersants or surfactants. The α,β-ethylenically unsaturated carboxylic acid also enables permeation of oxygen and moisture through the polymeric film which is desirable for maintaining healthy nails.

Component (3) of the nail polish composition is an acrylate ester. The acrylate ester has the formula $CH_2=CH—COOR_1$, wherein $R_1$ is $C_1-C_{20}$ alkyl, phenyl, benzyl, hydroxy-$(C_1-C_4)$-alkyl, $C_1-C_4$ alkoxy-$(C_1-C_4)$ alkyl, cyclopenyl, cyclohexyl, furyl, $C_1-C_4$ alkylfuryl, tetrahydrofuryl, or $C_1-C_4$ alkyltetrahydrofuryl. The acrylate ester is present in an amount of 8 to 75 weight percent, preferably 20 to 50 weight percent, based on the total weight of the nail polish composition. More than one acrylate ester may be used in the nail polish composition. Acrylate esters are used to modify the glass transition temperature, hydrophobicity, and rubbery characteristics of the film. Examples of acrylate esters include: methyl acrylate, ethyl acrylate, butyl acrylate, hexyl acrylate, isooctyl acrylate, isodecyl acrylate, lauryl acrylate, stearyl acrylate, phenoxyethyl acrylate, methoxyethyl acrylate, benzyl acrylate, furyl acrylate, methylfuryl acrylate, butylfuryl acrylate, tetrahydrofurfuryl acrylate, ethoxyethyl acrylate, 2-ethylhexyl acrylate, cyclopentyl acrylate, cyclohexyl acrylate, isobornyl acrylate, hydroxyethyl acrylate, and hydroxypropyl acrylate. Combinations of acrylate esters may also be used. Preferably the acrylate ester is selected from butyl acrylate, 2-ethylhexyl acrylate, 2-hydroxyethyl acrylate, and hydroxypropyl acrylate.

Component (4) of the nail polish composition is a methacrylate ester. The methacrylate ester has the formula $CH_2=C(CH_3)—COOR_2$, wherein $R_2$ is $C_1-C_{20}$ alkyl, phenyl, benzyl, hydroxy-$(C_1-C_4)$-alkyl, $C_1-C_4$ alkoxy-$(C_1-C_4)$ alkyl, cyclopentyl, cyclohexyl, furyl, $C_1-C_4$ alkylfuryl, tetrahydrofuryl, or $C_1-C_4$ alkyltetrahydrofuryl. The methacrylate ester is present in an amount of 8 to 75 weight percent, preferably 20 to 60 weight percent, based on the total weight of the nail polish composition. Methacrylate esters are used to modify the gloss, hydrophobicity, and glass transition temperature of the nail polish composition. Examples of methacrylate esters include: methyl methacrylate, ethyl methacrylate, propyl methacrylate, butyl methacrylate, hexyl methacrylate, cyclohexyl methacrylate, isodocyl methacrylate, lauryl methacrylate, stearyl methacrylate, isobornyl methacrylate, phenyl methacrylate, benzyl methacrylate, propylene glycol methacrylate, tetrahydrofurfuryl methacrylate, hydroxylethyl methacrylate, and hydroxypropyl methacrylate. Preferably the methacrylate ester is selected from methyl methacrylate, ethyl methacrylate, butyl methacrylate, hydroxyethyl methacrylate, and hydroxypropyl methacrylate.

Other monomers such as vinyl acetate and styrene in amounts between 0.0 and 40.0 weight percent may also be used to modify the glass transition temperature and hydrophobicity of the nail polish composition.

The glass transition temperature (Tg) of the nail polish compositions is in the range of −10° to 70° C., preferably 20° C. to 60° C. The glass transition temperature was determined using a differential scanning calorimeter (DSC).

Plasticizers and coalescing solvents normally used in nail polishes may be added to modify the film forming characteristics of the nail polish compositions. The amount of such plasticizers and coalescing solvents is well known in the art. Examples of plasticizers include: adipic esters, phthalate esters, isobutyrate esters, terephthalate esters, epoxidized butyl esters of fatty acids, epoxidized vegetable oils, and polymeric plasticizers. Specific plasticizers are: di-2-ethylhexyladipate or dioctyladipate (DOA), di-2-ethylhexylphthalate or dioctylphthalate (DOP), di-2-ethylhexylterephthalate (DOTP), dicyclohexylphthalate, diisononylphthalate, diisononylphthalate, n-butyl benzyl phthalate, 1,3-butylene glycol/adipic acid polyester, di($C_7$, $C_9$-alkyl)adipate, dialkyl phthalate derivatives where the alkyl group is $C_1$ to $C_{12}$, preferably $C_7$, $C_9$, or $C_{11}$, di-n-hexylazelate, di-hexylphthalate, diphenylphthalate, tricresol phosphate, benzyl benzoate, dibutyl phosphate, tributyl phosphate, tributoxy ethyl phosphate, triphenyl phosphate, butyl acetyl ricinoleate, glycerol acetyl ricinoleate, dibutyl phthalate, diethyl phthalate, dioctyl phthalate, dimethoxy ethyl phthalate, diisobutyl phthalate, diamyl phthalate, dibutyl glycolate, butyl stearate, triethyl citrate, tributyl citrate, tributyl acetyl citrate, 2-hexyl triethyl acetyl citrate, dibutyl tartarate, camphor, epoxidized butyl esters of linseed oil fatty acids, epoxidized linseed oil, epoxidized soya oil, propylene glycol adipate, 2,2,4-trimethyl-1,3--pentanediol diisobutyrate (TXIB), methylabietate, cumylphenylacetate, dibutoxyethyladipate, di-n-hexylazelate, gyceryltribenzoate, tri-n-butylcitrate, dioctylfumarate, triisononyltrimellitate, dioctylisophthalate, butyloleate, chlorinated paraffin, tricresylphosphate, and dibutylsebacate.

The solution polymerization is carried out batchwise in a reaction vessel by adding the monomers to at least one solvent in the presence of an initiator at elevated temperatures. The molecular weight of the nail polish composition, measured by Gel Permeation Chromatography (GPC) using poly(methyl methacrylate) as a standard, is 5,000 to 180,000, preferably 20,000 to 150,000. The polymerization temperature is generally between 50° C. and 130° C. for a period of 4 to 24 hours, but varies with solvent systems and type of initiator.

Suitable initiators for use in the solution polymerization include peroxides and/or azo compounds. In addition, a redox initiator system may be used. A useful redox initiator system is a peroxide or azo initiator used in conjunction with a reducing agent. Examples of reducing agents include: ascorbic acid, sodium sulphoxylate formaldehyde, sodium metabisulfite, thiosulfates, bisulphates, organic cobalt compounds, and amines, especially aromatic amines.

The choice of solvent affects the solubility and reactivity ratios of each of the components and determines the chain transfer constant during polymerization which affects the molecular weight and microstructure of the polymers. Nail polish formulations which are prepared using the compositions of this invention contain at least one water miscible solvent. In the case where the initiator does not dissolve in the water miscible solvent, at least one water immiscible co-solvent is recommended. Preferred water miscible solvents are acetone, isopropyl alcohol, n-propyl alcohol, propylene glycol monomethyl ether, and dipropylene glycol monomethyl ether. Preferred water immiscible co-solvents are methyl ethyl ketone, methyl propyl ketone, ethyl acetate, propyl acetate, butyl acetate, isobutyl acetate, and butyl alcohol.

After polymerization, the resulting solution polymers are subjected to shear, pressure, or other comminuting force in the presence of sufficient quantity of water and adequate amount of an amine to invert into the aqueous phase.

The brookfield viscosity of the aqueous nail polish compositions of this invention range from 50 to 800 cps, preferably 100 to 400 cps, which provides good flow and leveling without sagging. The rheology is controlled internally, that is, it is controlled by molecular weight, polymer concentration, and pH values. This is in contrast to emulsion nail polish compositions which require the use of thickening agents such as water-soluble cellulosics, polyacrylates, or water-swellable clays to adjust viscosity. Such thickening agents may create other problems in nail polish formulations such as water sensitivity of the final film.

The aqueous nail polish compositions disperse pigment like organic solvent resins without auxiliary dispersant or surfactant. This is attributed by the presence of the carboxylic functionalities in the polymers. In contrast to those emulsion polymers, it is known that pigmentation for emulsion polymers is usually very difficult and requires the addition of dispersant, defoamer, and/or wetting agent. Such additives usually increase water sensitivity and lower the gloss of the film.

The aqueous nail polish of the present invention will be further illustrated by a consideration of the following examples, which are intended to be exemplary of the invention.

EXAMPLE 1

Preparation of an aqueous acrylic resin of methacrylic acid, methyl methacrylate, and butyl acrylate crosslinked with difunctional acrylated urethane oligomer.

Into a three-neck reaction flask were placed 2.4 gram of methacrylic acid, 9.0 gram of methyl methacrylate, 7.6 gram of butyl acrylate, 145.0 gram of propylene glycol monomethyl ether and 30.0 gram of butyl acetate. The mixture was stirred and purged with nitrogen for thirty minutes while being heated to 80° C. to 95° C. and 1.5 gram of 97% benzoyl peroxide was charged into the reaction flask. After fifteen minutes, a mixture of 12.5 gram of Sartomer CN-953 difunctional acrylated urethane oligomer, which was analyzed as an adduct of dicyclohexylmethane 4,4'-diisocyanate, and 2-hydroxyethyl acrylate with a weight average molecular weight 7,000±300 and polydispersity 2.7, from Sartomer Co., 27.6 gram methacrylic acid, 103.5 gram methyl methacrylate, and 87.4 butyl acrylate were added into the reaction flask over a 150 minute period with additional 3.0 gram of 97% benzoyl peroxide. The reaction was post-cooked for five hours at 80° C. to 95° C. with an additional 2.0 gram of 97% benzoyl peroxide.

The resulting solution polymer was concentrated by removing 42 grams of solvent by distillation. The solution polymer was inverted into an aqueous solution polymer by mixing with an adequate amount of ammonium hydroxide and 510 gram water to convert the carboxylic acid groups into salts. This aqueous solution polymer was clear.

Weight average molecular weight was determined to be 83,000, Tg was 42° C. Brookfield viscosity was 190 cps, and total residual monomers were less than 0.01% by weight. The resulting polymer was softened by mixing with 8.1 grams of triethyl citrate.

EXAMPLE 2

Preparation of aqueous acrylic resin of methacrylic acid, methyl methacrylate, and butyl acrylate crosslinked with difunctional acrylated urethane oligomer.

Into a three-neck reaction flask was placed 1.6 gram methacrylic acid, 11.8 gram methyl methacrylate, 7.4 gram butyl acrylate, 155.0 n-propyl alcohol, and 35.0.gram ethyl acetate. The reaction mixture was stirred and purged with nitrogen for 30 minutes while being heated to 80° C. to 95° C., and then 1.5 gram benzoyl peroxide was charged into the reaction flask. After 15 minutes a mixture of 8.8 gram Sartomer CN-953 urethane difunctional acrylated oligomer, 18.4 gram methacrylic acid, 117.7 gram methyl methacrylate, and 85.1 gram butyl acrylate were added over a 150 minute period with additional 3.0 gram benzoyl peroxide. The reaction was continued for five hours at 80° C. to 95° C. with an additional 2.5 gram of benzoyl peroxide.

The resulting solution polymer was concentrated by removing 90 gram distillate and inverted into a aqueous solution polymer by mixing with an adequate amount of ammonium hydroxide and 525 gram water. The aqueous solution polymer was clear.

Weight average molecular weight was determined to be 38,000, Tg was 38.3° C., Brookfield viscosity was 360 cps, and total residual monomers were less than 0.01% by weight.

EXAMPLE 3

Preparation of an aqueous acrylic resin of methacrylic acid, methyl methacrylate, and butyl acrylate crosslinked with difunctional acrylated urethane oligomer.

Into a three-neck reaction flask were placed 8.0 gram methacrylic acid, 48.5 gram methyl methacrylate, 34.5 gram butyl acrylate, 5.0 gram hydroxyethyl acrylate, and 720.0 gram n-propyl alcohol. The mixture was stirred and purged with nitrogen for 30 minutes while being heated to 80° C. to 95° C., and then 8.6 gram of 70% benzoyl peroxide was added. After 15 minutes, a mixture of 50.0 gram Sartomer CN-953 urethane difunctional acrylated oligomer, 92 gram methacrylic acid, 57.5 gram of hydroxyethyl acrylate, 557.8 gram methyl methacrylate, and 62.7 gram of butyl acrylate was added over a 150-minute period with an additional 21.0 gram of 70% benzoyl peroxide in 180 gram butyl acetate. The reaction was followed by a five hour post-cook at 80° C. to 95° C. with an additional 10.8 gram of 70% benzoyl peroxide.

The resulting solution polymer was concentrated by removing 250 gram of distillate and converted into a aqueous solution polymer by mixing with an adequate amount of ammonium hydroxide and 3,050 gram water.

Weight average molecular weight was determined to be 108,000, Tg was 30.2° C. Brookfield viscosity was 304 cps, and total residual monomers were less than 0.01% by weight.

EXAMPLE 4

Preparation of aqueous acrylic resin of methacrylic acid, methyl methacrylate, and butyl acrylate crosslinked with difunctional acrylated urethane oligomer.

Into a three-neck reaction flask were placed 12.0 gram methacrylic acid, 45.0 gram methyl methacrylate, 39.0 gram butyl acrylate, and 720.0 gram n-propanol. The mixture was stirred and purged with nitrogen for 30 minutes while being heated to 80° C. to 95° C., and then 8:6 gram of 70% benzoyl peroxide was added. After 15 minutes, a mixture of 50 gram Sartomer CN-964, which was analyzed as an adduct of isophorone diisocyanate, hydroxyethyl acrylate, and neopentyl glycol with a weight average molecular weight of 3,250 ±150 and a polydispersity 2.1, 138.0 gram methacrylic acid, 517.5 gram methyl methacrylate, and 448.5 gram butyl acrylate were added over 150 minutes with an additional 21.0 gram of 70% benzoyl peroxide in 180.0 gram of butyl acetate. The reaction was post-cooked for five hours at 80° C. to 95° C. with an additional 10.8 gram of 70% benzoyl peroxide.

The resulting solution polymer was concentrated by removing 258 gram of distillate and inverted into a aqueous solution polymer by mixing with an adequate amount of ammonium hydroxide and 2,950 gram water. This aqueous solution polymer was clear.

Weight average molecular weight was determined to be 117,000, Tg was 49.4° C., Brookfield viscosity was 259 cps, and total residual monomers was less than 0.01% by weight. The resulting polymer solution was blended with 60 grams of diethyl phthalate.

EXAMPLE 5

Preparation of aqueous acrylic resin of methacrylic acid, ethyl methacrylate, and butyl acrylate crosslinked with difunctional acrylated urethane oligomer.

Into a three-neck reaction flask were placed 8.0 gram methacrylic acid, 61.0 gram ethyl methacrylate, 27.0 gram butyl acrylate, and 760 gram n-propyl alcohol. The mixture was stirred and purged with nitrogen for 30 minutes while being heated to 80° C. to 95° C., and then 10.0 gram of 70% benzoyl peroxide was charged into the reaction flask. After 15 minutes, a mixture of 50.0 gram Sartomer CN-953 difunctional acrylated urethane oligomer, 92.0 gram methacrylic acid, 701.5 gram ethyl methacrylate, end 310.5 gram butyl acrylate was added into the reaction flask over 150 minutes with an additional 20.0 gram of 70% benzoyl peroxide in 180.0 gram butyl acetate. This reaction was post-cooked for five hours at 80° C. to 95° C., and additional 12.0 gram of 70% benzoyl peroxide was charged during this period. Distillation was carried out at 97° C. to 100° C. to distill off 270 gram distillate.

The resulting solution polymer was inverted into a aqueous solution polymer by mixing with adequate amount ammonium hydroxide and 2,900 gram of water. The aqueous nail polish formulation was clear.

Weight average molecular weight was determined to be 155,000, Tg was 35.5° C., Brookfield viscosity was 279 cps, and total residual monomer as less than 0.01% by weight.

EXAMPLE 6

Preparation of pigmented aqueous nail polish.

A stable pigmented aqueous nail polish was prepared by mixing 15 gram of an OR-A-SPERSE RED 34,000-726 red pigment from Organic Pigments Corporation and 150 gram of the nail polish composition prepared in Example 1.

EXAMPLE 7

Preparation of aqueous acrylic resin of methacrylic acid, ethyl methacrylate, and butyl acrylate crosslinked with difunctional acrylated urethane oligomer.

Into a three-neck reaction flask were placed 15.0 gram methacrylic acid, 53.0 gram ethyl methacrylate, 8.5 gram butyl acrylate, and 290.0 gram n-propyl alcohol. The mixture was stirred and purged with nitrogen for 30 minutes while being heated to 90° C., and then 4.0 gram of 70% benzoyl peroxide was charged into the reaction flask. A mixture of 20.0 gram of Sartomer CN-953 difunctional acrylated urethane oligomer, 55.0 gram methacrylic acid, 187.0 gram ethyl methacrylate, and 161.5 gram butyl acrylate were added into the reaction flask over 150 minutes with an additional 6.5 gram of 70% benzoyl peroxide in 36.0 gram of acetone. The reaction was post cooked for five hours at 85° C. to 90° C. with an additional 6.5 gram of 70% benzoyl peroxide in 36.0 gram of acetone.

The resulting solution polymer was concentrated by azeotropic distillation wherein 4.0 gram of 28% ammonia and 130 gram of water were charged into the reaction flask, followed by azeotropic distillation under nitrogen at 82° C. to 87° C. to remove 150.0 gram of distillate. Additional 7.0 gram of 28% ammonia and 600 gram of water, and 0.05 gram of a defoamer AF-72 from General Electric Company were charged into the reaction flask, followed by azeotropic distillation at 78° C. to 86° C. under nitrogen to remove 120.0 gram of distillate. The solution was inverted into an aqueous solution by mixing with 13.0 gram of 28% ammonia and 300.0 gram of water.

Weight average molecular weight was determined to be 58,000, Tg was 34.7° C., and the Brookfield viscosity was 320 cps.

COMPARATIVE EXAMPLE 8

Preparation of an aqueous solution polymer of methacrylic acid, methyl methacrylate, and butyl acrylate without crosslinking with difunctional acrylated urethane oligomer.

Into a three-neck reaction flask were paced 2.4 gram methacrylic acid, 10.6 gram methyl methacrylate, 7.0 gram butyl acrylate, and 110.0 gram n-propanol. The reaction mixture was stirred and purged with nitrogen for 30 minutes while heated up to 80° C. to 95° C., 1.5 gram of 97% benzoyl peroxide was charged into the reaction flask. After 15 minutes, a mixture of 27.6 gram methacrylic acid, 121.9 gram methyl methacrylate, and 80.5 gram butyl acrylate was charged into the reaction flask over 150 minutes with additional 3.0 gram of 97% benzoyl peroxide. The reaction was post-cooked for six hours with additional 2.0 gram of 97% benzoyl peroxide.

The resulting solution polymer was concentrated by distilling off 81 gram distillate and inverted into aqueous solution polymer by mixing with adequate amount of ammonium hydroxide and 520 gram water. The aqueous solution polymer was clear.

Weight average molecular weight was determined to be 58,000, Tg was 44° C., Brookfield viscosity was 380 cps, and total residual monomers were less than 0.01% by weight.

EXAMPLE 9

Evaluations

A. Freeze-thaw stability—Aqueous nail polish compositions prepared in Examples 1–7 and Comparative Example 8 were placed into a freezer at −20° C. for 24 hours. The compositions were removed from the freezer and allowed to thaw at room temperature. Freeze-thaw cycle was repeated three times.

B. Heat aging stability—Aqueous nail polish compositions prepared in Examples 1–7 and Comparative Example 8 were placed into an oven at 50° C. for one week. Stability was evaluated by visual assessment and viscosity measurements.

C. Coatability—Aqueous nail polish compositions prepared in Examples 1–7 and Comparative Example 8 were brushed on nails of a group of healthy people. Ease of coating, leveling or sagging after coating, and skin irritation were evaluated by visual observation.

D. Gloss and gloss retention—Aqueous nail polish compositions prepared in Examples 1–7 and Comparative Example 8 were coated twice onto a Form 7B- Sag and Leveling test paper from the Leneta Company using a #4 bar. The coated test papers were allowed to stand for 60 minutes at 25° C. and a relative humidity of 40 to 60%. Gloss of the nail polish compositions was determined a 20° C. and 60° C. reflections by a lab reflectometer from DrLange Co., both initially and after five days.

E. Drying time—Aqueous nail polish compositions prepared in Examples 1–7 and Comparative Example 8 were coated onto a Form 7B—sag and leveling test paper using a #4 bar. A cotton ball was used to touch the compositions with a slight amount of pressure, and the dry time was the time that the cotton no longer stuck to the compositions. Dry to touch time was measured at 25° C. and relative humidity 40 to 60%.

F. Resistance to water/detergent and abrasion—Aqueous nail polish compositions prepared in Examples 1–7 and Comparative Example 8 were coated twice onto healthy human nails and were allowed to stand at room temperature for one hour. The coated human nails were dipped into 40° C. hot water containing 5.0% liquid detergent for 15 minutes, followed by rubbing 30 times with a paper towel. The degree of damage was assessed.

G. Adhesion and durability—Aqueous nail polish compositions prepared in Examples 1–7 and Comparative Example 8 were coated on nails of a group of healthy people. Adhesion and durability were assessed after three days.

TABLE I

PERFORMANCE EVALUATION

| Performance | Ex. 1 | Ex. 2 | Ex. 3 | Ex. 4 | Ex. 5 | Ex. 6 | Ex. 7 | Ex. 8 |
|---|---|---|---|---|---|---|---|---|
| Freeze-Thaw Stability | Pass | Pass | Pass | Pass | Pass | Pass | Pass | Pass |
| Heat-aging | Pass | Pass | Pass | Pass | Pass | Pass | Pass | Pass |
| Coatability | Good | Good | Good | Good | Good | Good | Good | Fair |
| Initial Gloss (20°/60°) | 64/89 | 69/89 | 68/88 | 66/88 | 68/87 | — | 66/88 | 56/85 |
| Gloss after 5 days (20°/60°) | 63/88 | 67/88 | 67/87 | 60/85 | 69/87 | — | 66/87 | 42/78 |
| Drying Time (sec) | 64 | 55 | 58 | 58 | 57 | 60 | 55 | 60 |
| Resistance to water/detergent | Good | Good | Good | Good | Good | Good | Good | Poor |
| Adhesion and durability | Good | Good | Good | Good | Good | Fair | Good | Poor |

The nail polish compositions of this invention dry quickly to form a high gloss film on nails. The film is clear and dries faster than conventional solvent based nail polishes. The nail polish compositions also give much better gloss and image clarity than corresponding emulsion nail polishes with similar compositions and concentrations. This is attributed to the fact that in emulsion polymers the polymer particles are dispersed in water and the polymer films are formed through coalescence of the particles, which usually results in lower reflection.

The aqueous nail polishes of this invention are freeze-thaw stable due to adequate concentrations of partially neutralized carboxylic groups. The aqueous nail polish compositions provide good adhesion to nails because of the polar functionalities, glass transition temperature and molecular weight.

Many variations will suggest themselves to those skilled in this art in light of the above detailed description. All such obvious modifications are within the full intended scope of the appended claims.

What is claimed is:

1. A nail polish composition comprising an aqueous solution containing an acrylic resin crosslinked with a difunctional acrylated urethane oligomer and having a solid level of 15 to 35 percent, a Tg of −10° C. to 70° C., and a weight average molecular weight of 5,000 to 180,000, which is prepared by solution polymerization of the following components:

(1) 0.1 to 15 weight percent of a difunctional acrylated urethane oligomer;

(2) 2 to 20 weight percent of an $\alpha,\beta$-ethylenically unsaturated carboxylic acid monomer containing 3 to 10 carbon atoms;

(3) 8 to 75 weight percent of an acrylate ester having the formula $CH_2=CH-COOR_1$, wherein $R_1$ is selected from the group consisting of $C_1-C_{20}$ alkyl, phenyl, benzyl, hydroxy-$(C_1-C_4)$-alkyl, $C_1-C_4$ alkoxy-$(C_1-C_4)$ alkyl, cyclopentyl, cyclohexyl, furyl, $C_1$–$C_4$ alkylfuryl, tetrahydrofuryl, and $C_1$–$C_4$ alkyltetrahydrofuryl; and (4) 8 to 75 weight percent of a methacrylate ester having the formula $CH_2=C(CH_3)$—$COOR_2$ wherein $R_2$ is selected from the group consisting of $C_1$–$C_{20}$ alkyl, phenyl, benzyl, hydroxy-($C_1$–$C_4$)-alkyl, $C_1$–$C_4$ alkoxy-($C_1$–$C_4$) alkyl, cyclopentyl, cyclohexyl, furyl, $C_1$–$C_4$ alkylfuryl, tetrahydrofuryl, and $C_1$–$C_4$ alkyltetrahydrofuryl;

wherein the aqueous solution is prepared by solution polymerization of said components at a temperature of 50° C. to 130° C. in the presence of at least one water miscible solvent and an initiator, to make solution polymers which are further processed in the presence of a sufficient quantity of water and an adequate amount of amine to invert into an aqueous phase, and the weight percents are based on the total weight of the nail polish composition.

2. A nail polish composition comprising an aqueous solution containing an acrylic resin crosslinked with a difunctional acrylated urethane oligomer and having a solid level of 15 to 35 percent, a Tg of $-10°$ C. to 70° C., and a weight average molecular weight of 5,000 to 180,000, which is prepared by solution polymerization of the following components:

(1) 2 to 10 weight percent of a difunctional acrylated urethane oligomer;

(2) 4 to 15 weight percent of an $\alpha,\beta$-ethylenically unsaturated carboxylic acid monomer containing 3 to 10 carbon atoms;

(3) 20 to 50 weight percent of an acrylate ester having the formula $CH_2=CH$—$COOR_1$, wherein $R_1$ is selected from the group consisting of $C_1$–$C_{20}$ alkyl, phenyl, benzyl, hydroxy-($C_1$–$C_4$)-alkyl, $C_1$–$C_4$ alkoxy-($C_1$–$C_4$) alkyl, cyclopentyl, cyclohexyl, furyl, $C_1$–$C_4$ alkylfuryl, tetrahydrofuryl, and $C_1$–$C_4$ alkyltetrahydrofuryl; and (4) 20 to 60 weight percent of a methacrylate ester having the formula $CH_2=C(CH_3)$—$COOR_2$ wherein $R_2$ is selected from the group consisting of $C_1$–$C_{20}$ alkyl, phenyl, benzyl, hydroxy-($C_1$–$C_4$)-alkyl, $C_1$–$C_4$ alkoxy-($C_1$–$C_4$) alkyl, cyclopentyl, cyclohexyl, furyl, $C_1$–$C_4$ alkylfuryl, tetrahydrofuryl, and $C_1$–$C_4$ alkyltetrahydrofuryl;

wherein the aqueous solution is prepared by solution polymerization of the components at a temperature of 50° C. to 130° C. in the presence of at least one water miscible solvent and an initiator, to make solution polymers which are further processed in the presence of a sufficient quantity of water and an adequate amount of amine to invert into an aqueous phase, and the weight percents are based on the total weight of the nail polish composition.

3. The aqueous nail polish composition of claim 1 wherein the difunctional acrylated urethane oligomer, component (1), is prepared by reacting an hydroxy acrylate or hydroxy methacrylate; a hydroxyl-terminated diol, polyester, or diamine; and a diisocyanate.

4. The aqueous nail polish composition of claim 1 wherein the $\alpha,\beta$-ethylenically unsaturated carboxylic acid monomer, component (2), is selected from the group consisting of acrylic acid, methacrylic acid, crotonic acid, fumaric acid, itaconic acid, maleic anhydride, and combinations thereof.

5. The aqueous nail polish composition of claim 4 wherein the $\alpha,\beta$-ethylenically unsaturated carboxylic acid monomer is selected from the group consisting of acrylic acid, methacrylic acid, and maleic anhydride.

6. The aqueous nail polish composition of claim 1 wherein the acrylate ester, component (3), is selected from the group consisting of methyl acrylate, ethyl acrylate, butyl acrylate, hexyl acrylate, isooctyl acrylate, isodecyl acrylate, lauryl acrylate, stearyl acrylate, phenoxyethyl acrylate, methoxyethyl acrylate, benzyl acrylate, furyl acrylate, methylfuryl acrylate, butylfuryl acrylate, tetrahydrofurfuryl acrylate, ethoxyethyl acrylate, 2-ethylhexyl acrylate, cyclopentyl acrylate, cyclohexyl acrylate, isobornyl acrylate, hydroxyethyl acrylate, hydroxypropyl acrylate, and combinations thereof.

7. The aqueous nail polish composition of claim 6 wherein the acrylate ester is selected from the group consisting of butyl acrylate, 2-ethylhexyl acrylate, 2-hydroxyethyl acrylate, and hydroxypropyl acrylate.

8. The aqueous nail polish composition of claim 1 wherein the methacrylate ester, component (4), is selected from the group consisting of methyl methacrylate, ethyl methacrylate, propyl methacrylate, butyl methacrylate, hexyl methacrylate, cyclohexyl methacrylate, isodocyl methacrylate, lauryl methacrylate, stearyl methacrylate, isobornyl methacrylate, phenyl methacrylate, benzyl methacrylate, propylene glycol methacrylate, tetrahydrofurfuryl methacrylate, hydroxylethyl methacrylate, hydroxypropyl methacrylate, and combinations thereof.

9. The aqueous nail polish composition of claim 8 wherein the methacrylate ester is selected from the group consisting of methyl methacrylate, ethyl methacrylate, butyl methacrylate, hydroxyethyl methacrylate, and hydroxypropyl methacrylate.

10. The aqueous nail polish composition of claim 1 which additionally contains 0.1 to 40 weight percent of a vinyl monomer.

11. The aqueous nail polish composition of claim 1 which additionally contains 0.1 to 40 weight percent of styrene.

12. The aqueous nail polish composition of claim 1 wherein the water miscible solvent is selected from the group consisting of acetone, isopropyl alcohol, n-propyl alcohol, propylene glycol monomethyl ether, dipropylene glycol monomethyl ether, and combinations thereof.

13. The aqueous nail polish composition of claim 12 wherein the water miscible solvent is selected from the group consisting of acetone, isopropyl alcohol, n-propyl alcohol, propylene glycol monomethyl ether, and dipropylene glycol monomethyl ether.

14. The aqueous nail polish composition of claim 1 which additionally contains a water immiscible co-solvent selected from the group consisting of methyl ethyl ketone, methyl propyl ketone, ethyl acetate, propyl acetate, butyl acetate, isobutyl acetate, butyl alcohol, and combinations thereof.

15. The aqueous nail polish composition of claim 1 wherein the initiator is selected from the group consisting of a peroxide, an azo compound, and combinations thereof.

16. The aqueous nail polish composition of claim 1 wherein the initiator comprises an oxidizing agent and a reducing agent.

17. The aqueous nail polish composition of claim 1 which additionally comprises at least one additive selected from the group consisting of pigments, dyes, fragrances, plasticizers, UV stabilizers, antioxidants, and fillers.

* * * * *